(12) United States Patent
Li et al.

(10) Patent No.: US 7,999,936 B1
(45) Date of Patent: Aug. 16, 2011

(54) COMBINED TRANSMITTANCE AND ANGLE SELECTIVE SCATTERING MEASUREMENT OF FLUID SUSPENDED PARTICLES FOR SIMULTANEOUS DETERMINATION OF REFRACTIVE INDEX, EXTINCTION COEFFICIENT, PARTICLE SIZE AND PARTICLE DENSITY

(75) Inventors: Guoguang Li, Fremont, CA (US); Abdul Rahim Forouhi, Cupertino, CA (US); Erik Nackerud, Campbell, CA (US)

(73) Assignee: n&k Technology, Inc., San Jose, CA (US)

( * ) Notice: Subject to any disclaimer, the term of this patent is extended or adjusted under 35 U.S.C. 154(b) by 228 days.

(21) Appl. No.: 12/417,606

(22) Filed: Apr. 2, 2009

Related U.S. Application Data

(60) Provisional application No. 61/042,238, filed on Apr. 3, 2008.

(51) Int. Cl.
*G01N 15/02* (2006.01)
(52) U.S. Cl. .................. 356/336; 356/338; 356/343
(58) Field of Classification Search .......... 356/335–343, 356/73
See application file for complete search history.

(56) References Cited

U.S. PATENT DOCUMENTS

| | | | |
|---|---|---|---|
| 4,905,170 A | | 2/1990 | Forouhi et al. |
| 6,091,494 A | * | 7/2000 | Kreikebaum ............... 356/336 |
| 2003/0223063 A1 | * | 12/2003 | Hill et al. ..................... 356/340 |
| 2004/0075056 A1 | * | 4/2004 | Bell et al. ..................... 250/341.1 |

OTHER PUBLICATIONS

Swanson et al, "Limits of optical transmission measurements with application to particle sizing techniques" Applied Optics, 38, p. 5887, 1999.
Nefedov et al, "Analysis of particle sizes, concentration, and refractive index in measurement of light transmittance in forward-scattering-angle range" Applied Optics, 36, p. 1357, 1997.
C. F. Boren and D. R. Huffman, "Absorption and Scattering of Light by Small Particles, Wiley, New York, 1983".
Ferri et al, "Method version of the Chahine algorithm to invert spectral extinction data for particle sizing" Applied Optics, 34, p. 5829, 1995.

* cited by examiner

*Primary Examiner* — Hoa Q Pham
(74) *Attorney, Agent, or Firm* — Lumen Patent Firm (57) ABSTRACT

The refractive index, extinction coefficient, size and density of fluid suspended particles are simultaneously determined by combined transmittance and scattering measurements. The scattering measurements are preferably angle selective to obtain additional information about the scattered light. A charge-coupled device is employed for its high sensitivity to low light intensity in measurement of scattered light in combination with a photodiode array employed for its high signal to noise ratio, which is beneficial in transmittance measurement. The scattered light may be measured in an angle selective fashion by use of a motorized aperture that is concentrically positioned with respect to the impinging beam axis and moveable along the impinging beam axis. An ellipsoidal mirror collects the scattered light that passes through the motorized aperture and focuses the scattered light towards the charge-coupled device.

4 Claims, 10 Drawing Sheets

COMBINED TRANSMITTANCE AND ANGLE SELECTIVE SCATTERING MEASUREMENT OF FLUID SUSPENDED PARTICLES FOR SIMULTANEOUS DETERMINATION OF REFRACTIVE INDEX, EXTINCTION COEFFICIENT, PARTICLE SIZE AND PARTICLE DENSITY

PRIORITY CLAIM

The present Utility Application claims priority to and from the Provisional Application of the same Title and Inventors filed on 03-APR-2008 with Application No. 61/042,238 filed Apr. 3, 2008.

FIELD OF INVENTION

The present invention relates to methods and apparatus for combined transmittance and scattering measurements of fluid suspended particles for simultaneous determination of refractive index n, extinction coefficient k, particle size and particle density (number of particles per volume). In particular, the present invention relates to methods and apparatus for determination of n, k, particle size and particle density by combined use of a photodiode array detector for transmittance measurement and a charge-coupled device detector for scattering measurement.

BACKGROUND OF INVENTION

Optical techniques for remotely characterizing fluid suspended particles are receiving increased attention in the industry because they are highly suitable for high quality measurements in a non invasive and quasi real time fashion. Most common are transmittance based measurement techniques, in which light is directed through the fluid and the directly emitting remaining portion of the incident light is used to characterize the suspended particles. Transmittance based measurement techniques are less sensitive to noise especially at short wavelengths in the UV regime but are well suitable to obtain information about particles. However, information about particle sizes and particle distributions, and n and k are difficult to obtain with transmittance measurement alone as is well known in the art. This is mainly due to the strong correlations between n, k, size, and density of particles in the analysis. For example, increasing the particle density has a similar effect, to certain extent, as increasing the particle size to the transmittance spectra. Therefore, there exists a need for an optical measurement technique for fluid suspended particles that is capable of providing information about particle sizes and particle distributions. The present invention addresses this need.

Increasing attention has been received lately regarding scattered light measurement techniques to derive information about fluid suspended particles. In combination with well known mathematical algorithms and methods that are preferably computationally implemented, light scattering measurements may require relatively small optical design effort while providing highly accurate measurement results. A low number of lenses, mirrors and optical fibers are employed to direct a broadband spectral light source onto the fluid suspended particles and collect and direct the scattered light towards a detector. Also, the measurement has characteristics that can be computationally analyzed to determine particle size and n and k. One such well known characteristic is a wavelength dependent oscillation of the scattered light. From such oscillations, n and k may be roughly computationally determined.

Unfortunately, scattering oscillations decrease with particle size such that at approximately 0.2 μm particle sizes and below, n and k cannot be reliably determined from the scattered light at a fixed scattering angle. Therefore, there exists a need for an optical measurement technique for fluid suspended particles that provides information of n and k of particles also substantially below 0.2 μm size. The present invention also addresses this need.

In the prior art, scattered light is detected either by a single stationary or a single moveable detector or a number of stationary detectors. The more scattered light is detected as a function of angle, the more information about the suspended particles may be derived. Of particular interest are variations of the scattered light in relation to the scattering angle. Such variations can be detected in a continuous fashion over an extended scattering angle range. Prior art stationary detector(s) to the contrary provide simultaneous detection of only a fraction of the scattered light near a given scattering angle. Prior art moveable detectors may be continuously moved around the scatter origin but only along a linear path, which amounts also only to a small fraction of the total scattered light within a predetermined measurement range. Also, a moveable detector or a configuration for variable angle detection may require extensive design effort. Therefore, there exists a need for a method and apparatus capable of simultaneously detecting a substantial portion of the total scattered light along a predetermined scattering angle. The present invention also addresses this need.

Analyzing raw measurement data of transmittance spectra and scattering spectra is well known in the art. There are dispersion models such as Forouhi-Bloomer (U.S. Pat. No. 4,905,170), Cauchy, or others commonly implemented to reduce the number of variables. Other parameters in conjunction with basic formulations to perform calculations based on Beer-Lambert (BL) law are taught for example in Swanson et al, Applied Optics, 38, p. 5887, 1999; Nefedov et al, Applied Optics, 36, p. 1357, 1997, Furthermore, the extinction cross section of a single particle is also known to be calculated from Mie scattering theory as taught, for example in C. F. Boren and D. R. Huffman, "Absorption and Scattering of Light by Small Particles, Wiley, New York, 1983". Also, single scattering conditions in the transmittance of fluid suspended particles are for example, taught in Swanson et al, Applied Optics, 38, p. 5887, 1999. Also, it has been noticed in experiments that some forward scattered light may also be detected as transmitted light like in Nefedov et al, Applied Optics, 36, p. 1357, 1997. All prior art address some isolated issues relating to analyzing fluid suspended particles, but fail to teach a combination of detector choice and apparatus setup, and fail to teach a relevant analytical solution to address the need for simultaneously determining refractive index, extinction coefficient, particle size and particle density. The present invention also addresses this need.

SUMMARY

Broadband spectral light is directed towards a target area within a vessel that contains particles suspended in fluid. Particles present at the target scatter a portion of the impinging light in a fashion that highly depends on the particles' size, distribution and refractive index. A portion of the impinging light that is not absorbed or scattered by the suspended particles, propagates directly through the vessel and is detected by a first detector and recorded as transmittance spectrum T. The scattered light is detected by a second detector positioned at a suitable position with respect to the direction of the impinging light and recorded as scattering spectrum or spectra S. The raw transmittance T and scattering S data are then computationally analyzed preferably in a simultaneous iterative fashion to derive refraction index n and extinction coefficient k particle size and particle density. In an alternate approach, n and k and size may also be determined from the S alone. Once n and k are known, the particle size and density may be computed from T alone.

In a first embodiment, a photodiode array (PDA) detector was employed as first detector and a charge-coupled device (CCD) detector was employed as second detector. The PDA detector with its high signal to noise ratio and high pixel well depth was best suited for detecting the transmitted light. The CCD detector to the contrary with its high sensitivity to low light intensity provided satisfactory detection of the scattered light which commonly is much lower in intensity compared to the transmitted light. The combination of PDA detector for transmittance measurement and CCD detector for scattering measurement supplemented each other favorably resulting in an increased data output over a wavelength range that would be unobtainable if only a single type detector would be employed.

To ensure single scattering while obtaining sufficient signal from particles, the particle density and optical path length of the selected vessel was approximated such that the measured transmittance T after normalization was in the range of 10–80% for all wavelengths. The path length may be adjusted by vessel size, to get optimized T. On the other hand, the density of particles may be changed by diluting the fluid in which they are suspended. By warranting this well known single scattering, well known physical models including Mie's scattering theory and Beer-Lambert law computation of n and k, particle size and density was accurately achieved. Due to the broad data made available by combining PDA transmittance detection and CCD scatter detection, initial assumptions and iterative computation could be kept to a minimum resulting in fast and highly accurate results.

Further more, angle selective detection of the scattered light may be accomplished by a motored aperture preferably concentrically positioned around the axis of the impinging light. The motored aperture may be axially adjustable with respect to the impinging light axis. The motored aperture may shield all but a predetermined angular portion of the scattered light from reaching a surrounding mirror, which reflects the scattered light towards the second detector. By moving the aperture while light impinges the suspended particles, the scattered light may be detected selectively with respect to its scattering angle. The concentrically arranged motored aperture and surrounding mirror capture a substantial portion of the scattered light. Correlating the position of the motored aperture to the simultaneously detected scattered light provides for a profile of the scattered light with respect to the entire scattering angle range covered by the mirror and the motored aperture. As a favorable result, scattering angle specific intensity of the scattered light may be obtained with high accuracy and utilized as an additional parameter for measurement of n and k, particle size and particle density

DETAILED DESCRIPTION

Figure 1:
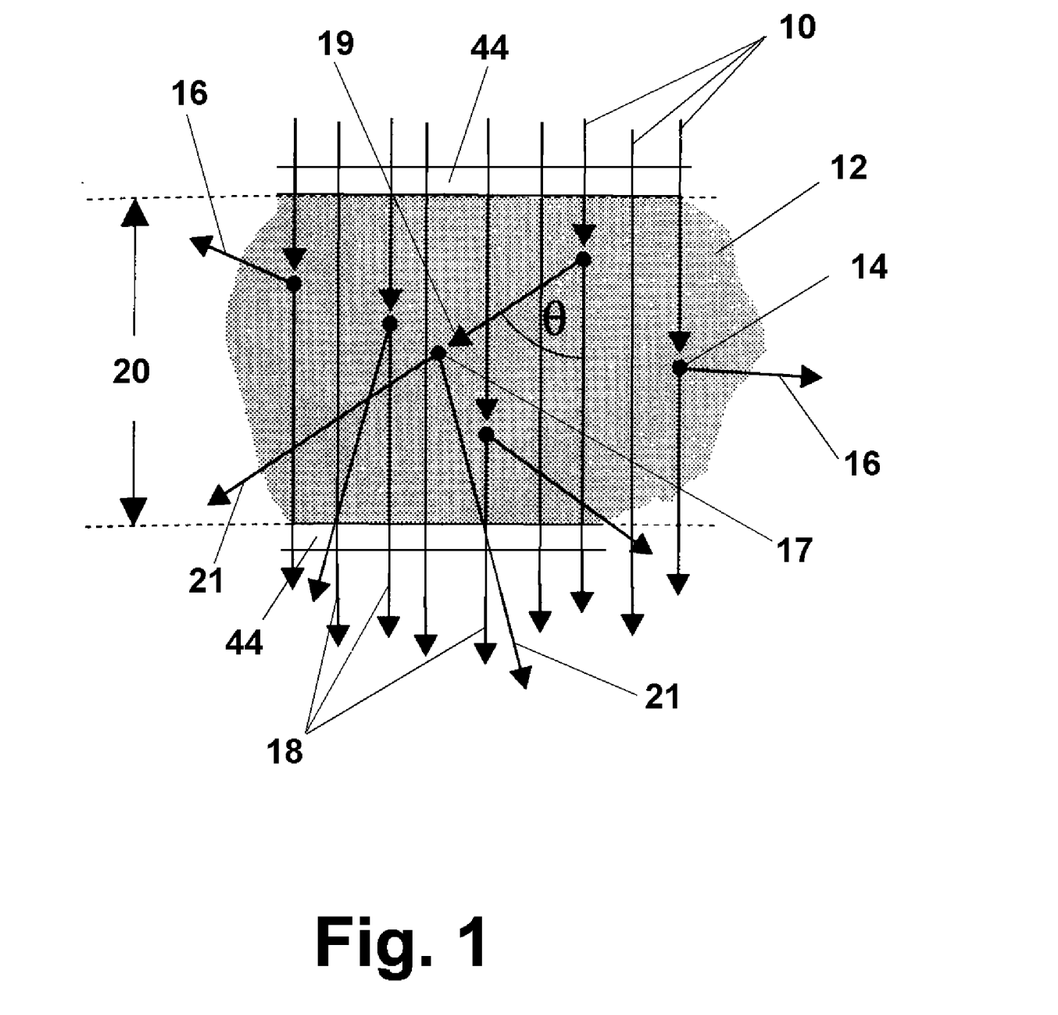
FIG. 1 is a schematic depiction of scatter S and transmittance T of light impinging on particles suspended in fluid.

Referring to FIG. 1, light 10 impinging on fluid 12 may pass directly through without being scattered or absorbed by particles 14 suspended in the fluid 12. This directly through transmitted light 18 may be detected and compared to the impinging light 10 to determine the transmittance T. A portion of the impinging light 10 interacts with the particles 14, in which it is absorbed or scattered at scattering angle θ. The scattering angle θ is between 0 and 180 degrees. When scattering angle is close to 180 degrees the scattered light is referred to as backscattering. The optical path length 20 is the distance within which the impinging light 10 interacts with suspended particles 14. Single scattering occurs when the scattered light 16 emerges from the fluid without interacting again with another particle 14. Multiple scattered light 21 occurs when initially scattered light 19 interacts again with a particle 17 before emerging again from the fluid 12. A portion of the scattered light 16, 21 may be captured and measured. The larger the portion of the angle resolved scattered light that is measured, the more accurate and detailed the scatter measurement may be. Single scattered light 16 and multiple scattered light 21 are not easily distinguishable in the measurement. To avoid ambiguous interpretation of the scatter measurement, it is desirable to minimize multiple scattered light 21. The fluid 12 is confined by the vessel 44 within the pass length 20.

In the present invention, multiple scattered light 21 is substantially avoided by selecting the optical path length 20 in conjunction with an approximated density of the suspended particles 14 such that at least 10% of the impinging light 10 is detected as transmitted light 18.

Figure 2:
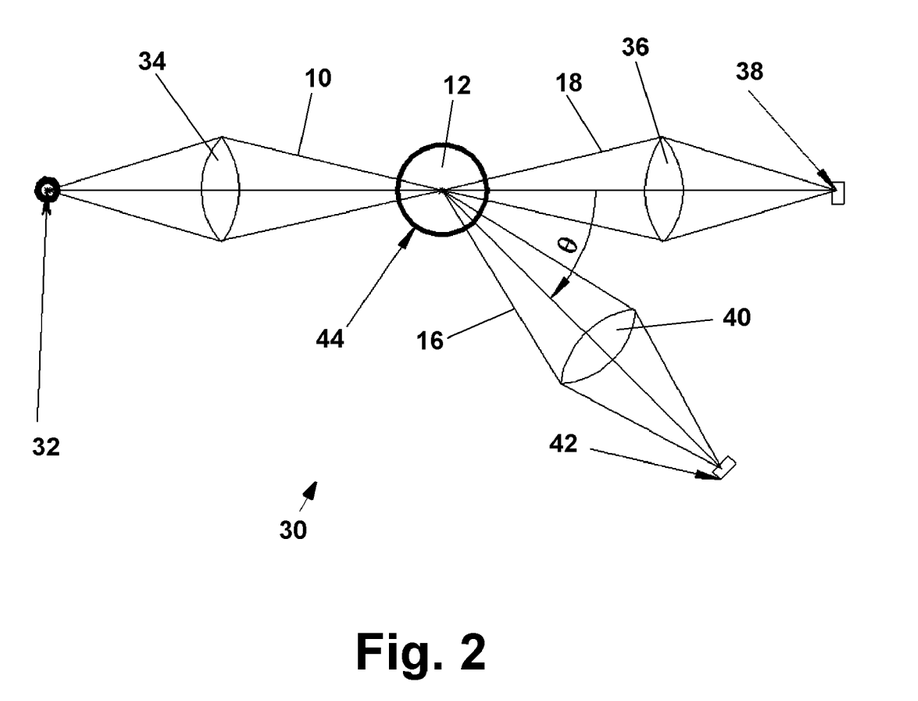
FIG. 2 schematically illustrates a combined PDA transmittance detection and CCD scatter detection.

Referring to FIG. 2, a particle characterization system 30 in general may include a broadband light source 32, a light delivering component 34, a vessel 44 to hold fluid 12, a first and second light collection component 36, 40 and first and second detectors 38, 42. The vessel may be made of fused silica, glass or any other optically transparent material for the desired measurement wavelength range with preferably a cylindrical or better spherical curvature at least within the penetration area of the impinging light 10, transmitted light 18 and scattered light 16.

The impinging light 10 may be polarized or un-polarized light. For that purpose, a well known polarizer (not shown in FIG. 2) may be used to create polarized light from un-polarized light source 32. The polarizer may be rotated mechanically or electrically dependent on polarizer type and design. In this case, Eq. 3 should be changed accordingly and is well known in the art.

The fluid 12 is preferably chosen to substantially and statically suspend the particles 14 at least during the measurement process. The first detector 38 may be specifically configured for transmittance measurement preferably utilizing a well known PDA sensor including well known CMOS and NMOS sensors that are advantageous with their large dynamic range and high signal-to-noise ratio for detecting high intensity light.

The second detector 42 may be specifically configured for scatter measurement utilizing a well known CCD (including back-thinned) imaging sensor that is naturally integrating the receiving light over time and is more sensitive and better for low intensity light detection. Scattered light 16 may amount to about 0.001% or less of the impinging light 10, whereas transmitted light 18 amounts at least to 10% of the impinging light 10, which is five orders of magnitude higher than the scattered light 16. Due to this large difference between scattered light 16 and transmitted light 18, selection and configuration of sensors 38, 42 and collection systems 36, 40 is important to retrieve raw S and T data that can be unambiguously analyzed.

Nevertheless, the present invention may include embodiments in which both detectors 38, 42 utilize CCD sensors. A CCD sensor may be adjusted with shutter speed and other well known means to the intensity of the transmitted light 18. Using the same type of sensors for both S and T may greatly reduce design effort of a combined S and T measurements apparatus as will be explained further below.

Figure 3:
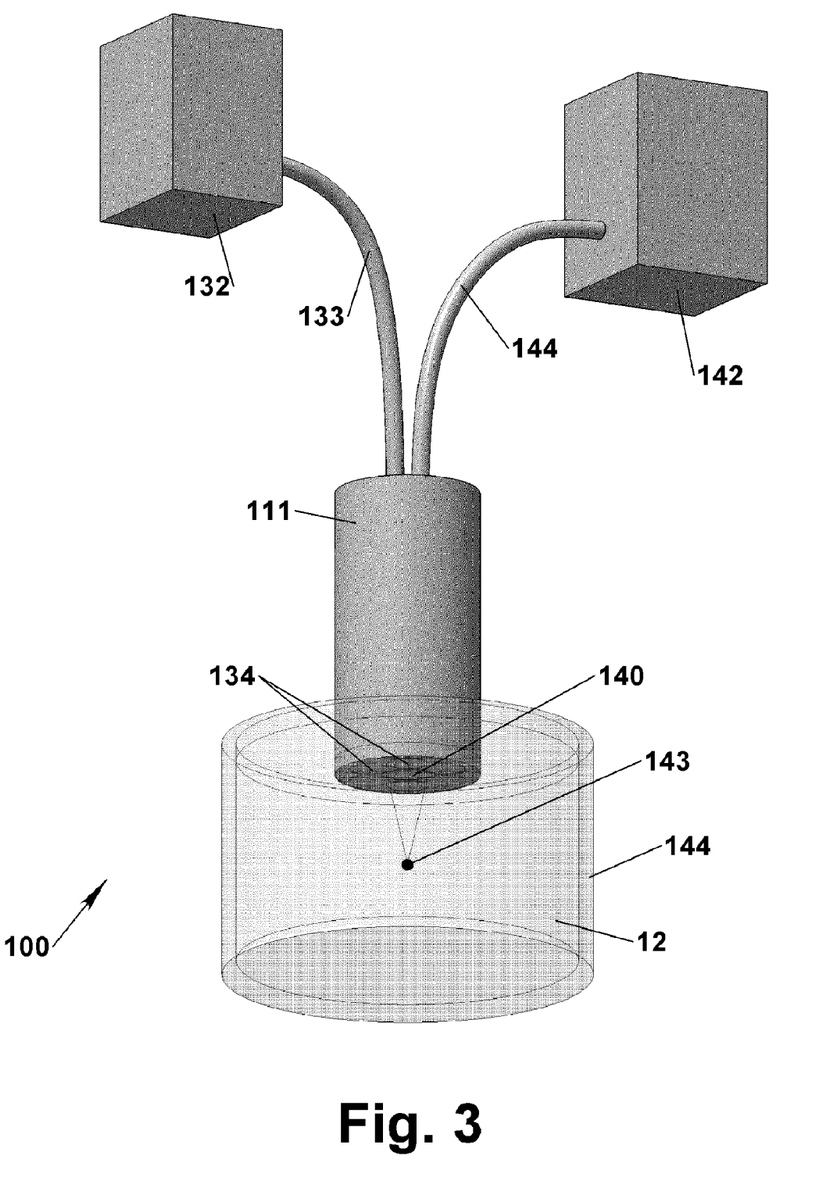
FIG. 3 is a schematic depiction of representative apparatus for backscattering detection.

Referring to FIG. 3 and in accordance with a first embodiment of the invention, a system 100 for detection of backscattered light 16 as shown in FIG. 1, was configured with a CCD spectrometer, for example USB4000™ 142, and a probe 111 all commercially available from Ocean Optics Inc. The scatter probe 111 featured a central collection fiber 140 with 200 µm in diameter and a numerical aperture of 0.22, within which backscattered light 16 was captured while the probe 111 was immersed in the fluid 12. Six illumination fibers 134 also having a 200 µm diameter surrounded the central collection fiber 140.

Broadband light provided by the white light source 132 was passed via fiber 133 to the probe 111. The captured scattered light 16 was guided via fiber 144 to the spectrometer 142 for measurement. The captured scattered light 16 was passed through a 25 µm wide slit at the entrance of the spectrometer 142.

Figure 4:
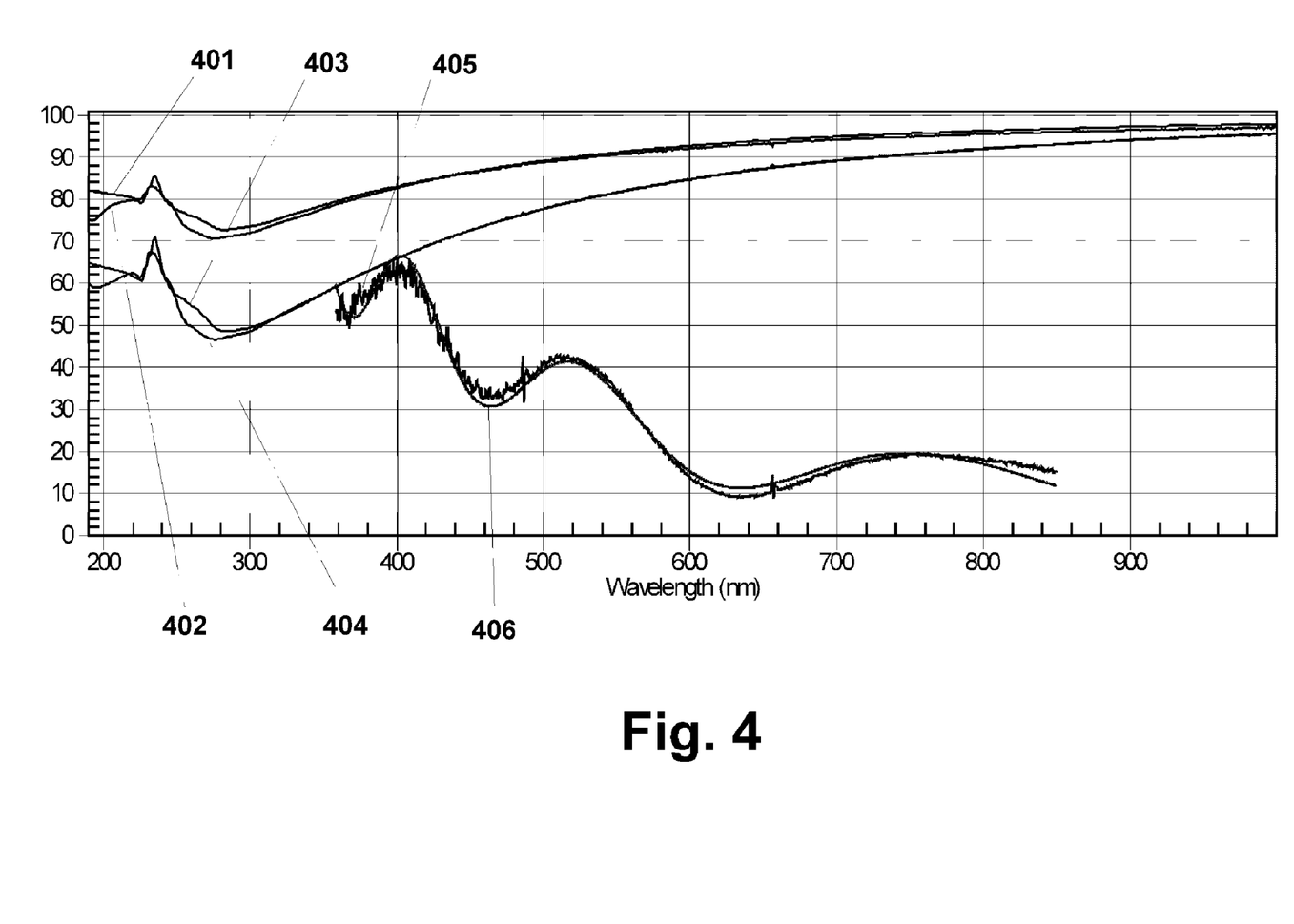
FIG. 4 is a graph of measured versus computationally curve fitted T and S spectra.

In the first embodiment, fluid 12 including the suspended particles 14 was transferred into two vessels 44 of 0.5 mm and 0.2 mm optical path length for measurements of their respective transmittance spectra. The transmitted light 18 was measured with an Agilent 8453™ transmittance measurement spectrometer. The transmittance spectrometer was configured with a 50 µm slit. Polystyrene Latex (PSL) particles with 0.5 µm from Duke Scientific™ were diluted in DI water to provide the suspended particles 14. The S measurement was performed by use of the configuration described above in reference to FIG. 3. Measurements of T and S are depicted in FIG. 4. Curves 402, 404 are the measured normalized transmittance intensities with the 0.2 mm and 0.5 mm vessels 44 over a wavelength range of 190 nm and 1000 nm.

The curve 405 illustrates the intensity of the backscattered light 16 captured at near 180 degree scatter angle θ. The S measurement becomes increasingly noisy with smaller wavelength, making its interpretation increasingly ambiguous. T measurement to the contrary has very low noise across the entire measurement spectrum but only significant intensity oscillations in the small wavelength range substantially below 380 nm. The S measurement to the contrary had substantial intensity oscillations along the entire measurement spectrum with increasing noise towards the UV spectrum. By using a well known back-thinned CCD detector with much better UV sensitivity, the S measurement may be extended to smaller wavelengths. The graph clearly shows the favorable combination of T and S measurements and their particular intensity oscillations to derive high content raw measurement data that is highly suitable for non-ambiguous interpretation and accurate analysis.

During analysis of the measurement data, multiple transmittance spectra with different particle densities and/or different optical path lengths 20 and scattering spectra with different scattering angles θ are preferably analyzed together. The particle intrinsic properties such as n, k and diameter are set as the same in the calculations for different spectra. Well known dispersion models such as Forouhi-Bloomer, Cauchy, or others are implemented to reduce the number of variables. The analysis is started with an initial assumption for parameters including size, density and dispersion of the particles 14. Other parameters in conjunction with the following basic formulations are also applied to perform the calculations based on the below Equations (1) and (2). From Beer-Lambert (BL) law we have $$T(\lambda) = I_t(\lambda)/I_o(\lambda) = \exp[-\tau(\lambda)] = \exp[-NC_{ext}(n,k,d,\lambda)L] \quad (1)$$

Where $I_t$ is the transmitted intensity for particles in liquid, $I_o$ is the transmitted intensity for pure liquid with the same vessel but without particles, N is density of particles 14 in liquid fluid 12 (number of particles per volume), $C_{ext}$ (n, k, d, λ) is the extinction cross section of a single particle 14 calculated from Mie scattering theory which is a function of n, k, wavelength, and diameter of the particle 14, and L is the optical path length 20 in the liquid in transmittance measurement.

BL law has assumed single scattering in the transmittance, which is the case when $-\ln T$ is smaller than 4.

The scattered light 16, S(λ, θ), can also be collected in the measurement, which is connected to the complex scattering amplitude function, s(λ, n, k, d, θ), in Mie calculation, $$S(\lambda,\theta) = Is(\lambda,\theta)/Io(\lambda) = B^*|s(\lambda,n,k,d,\theta)|^2 + A^*\exp(-C^*\lambda) \quad (2)$$

Where θ is the scattering angle, which is defined to be 0 at forward scattering and 180 at backward scattering direction, Io(λ) is the normalization spectrum collected either directly from the source or from a flat surface that gives a uniform reflectance, such as quartz, Is (λ, θ) is the scattered light collected at angle θ. This measurement is relative. A, B, C are adjustable parameters. $A^*\exp(-C^*\lambda)$ is used to account for the diffuse scattering, and s(λ, n, k, d, θ) is the complex scattering amplitude function given by Mie calculation. Clearly, the measured S (λ, θ) is still relative and cannot be used to determine the absolute number or density of particles. For un-polarized light and spherical particles, $$|s(\lambda,n,k,d,\theta)|^2 = [\lambda/(2\pi)]^2 * 0.5(|S1|^2 + |S2|^2) \quad (3)$$

Where S1 and S2 are the amplitude functions for the two orthogonally polarized E vectors as are well known in the art.

Here again single scattering is assumed, which means the light that is collected is only scattered once by the particles 14.

When A=0 and B=1, one can run simulations and see the angular and wavelength dependence of the scattering from free particles 14.

In most experiments, some forward-scattered light 16 is also recorded as transmitted light 18. Therefore, $C_{ext}$ (n, k, d, λ) in Eq. 1 should be replaced by $$C_{ext}(n,k,d,\lambda) - 2\pi \int |s(\lambda,n,k,d,\theta)|^2 \sin\theta\, d\theta$$

The integral is from 0 to the maximum collection angle in T.

Figure 5:
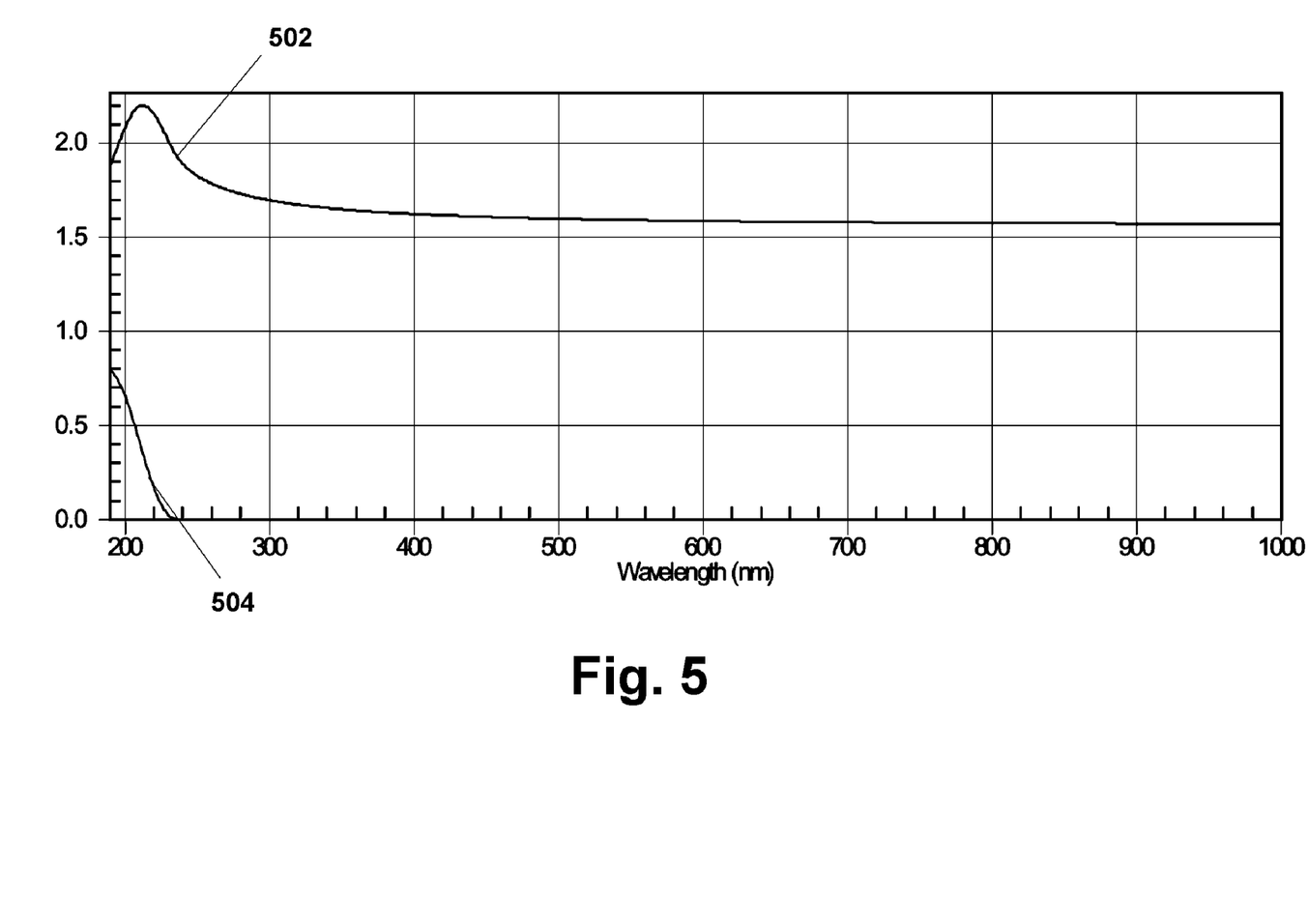
FIG. 5 is a graph of n and k derived from the measured T and S of FIG. 4.

The calculated spectrum fitted to the measured spectrum example are superimposed in FIG. 4 represented by spectra 401 and 403. The fitted backscattering spectrum is depicted by 406. In FIG. 5, extracted n is illustrated by curve 502 and extracted k is shown by curve 504.

In the above example, the determined parameters are listed in below Table 1:

TABLE 1

| Parameters | Diameter (μm) | n@589 nm | Density (×10$^9$/ml) |
|---|---|---|---|
| Calculated (from measurements) | 0.49 | 1.59 | 2.6 (0.2 mm vessel), 2.3 (0.5 mm vessel) |
| Nominal (from vender) | 0.50 | 1.59 | 2.5 |

Figure 6:
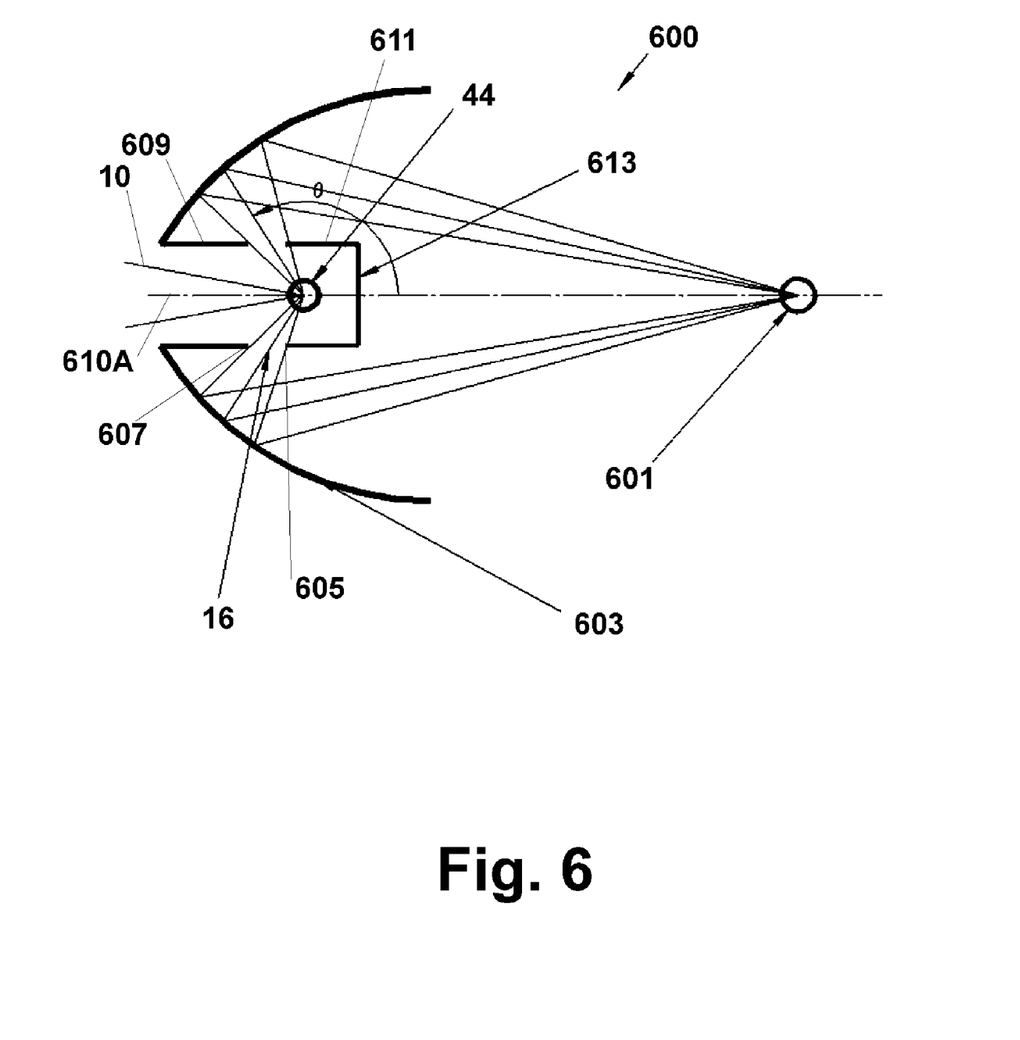
FIG. 6 shows a schema of an apparatus including a motored ring aperture for T and S measurements with a single detector.

An apparatus 600 for combined angle selective scattering measurement and transmittance measurement with a single T and S detector in accordance with a second embodiment of the invention is depicted in FIG. 6. In apparatus 600, the impinging light beam 10 is concentrically surrounded by a motored aperture 609, 611. The first and second aperture segments 609 and 611 may be combined and/or independently moved along the axis 610A. Movement of the aperture segments 609, 611 offsets their respective aperture edges 607, 605 providing a cylindrical opening that is concentric with respect to the impinging light beam 10 and the vessel 44. The cylindrical opening has a varying height that may be remotely controlled via the motored aperture segments 609, 611. Scattered light 16 may propagate only through the variable opening in a predetermined scattering angle, θ, its range, Δθ.

The scattered light 10 passing through the cylindrical opening impinges on an ellipsoidal mirror 603, in the following preferred configuration. The ellipsoidal mirror 603 is positioned such that its first focal point coincides with the focal point of the impinging light beam 10 and the vessel 44. At the second focal point of the ellipsoidal mirror 603, an optical receiver 601 in the form of an optical fiber end may be placed to receive the scattered light 16 and to direct it further towards a sensor. Alternatively an optical element(s) such as a lens or mirror may be appropriately placed in order to collect light from the second focal point, as may be well appreciated by anyone skilled in the art. The combination of the concentrically arranged mirror 603 and the concentrically arranged aperture segments 609, 611 allows all of the light 16 scattered in a predetermined angle θ and predetermined range Δθ around the axis 610A to be substantially collected for measurement.

The optical receiver or collecting components 601 is preferably positioned on and aligned with the optical axis 610A. A selectively removable door 613 may be opened such that transmitted light 18 may be directly captured by the light receiver 601 while the moveable apertures 609, 611 are closed. As a favorable result, T and S may be measured with a single spectrometer in well known optical communication with the light receptacle 601. Such single spectrometer may preferably be a CCD detector.

Figure 7:
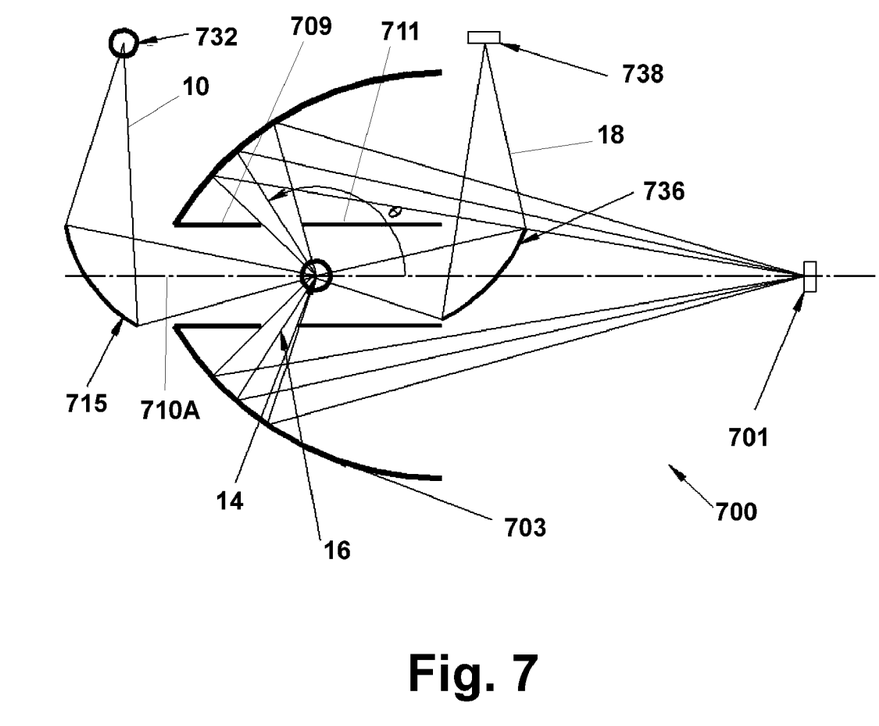
FIG. 7 depicts a schema of the apparatus of FIG. 6 configured for simultaneous T and S measurements with two detectors.

An apparatus 700 for combined angle selective scattering measurement and transmittance measurement with a separate T and S detector, in accordance with a third embodiment of the invention, is depicted in FIG. 7. Apparatus 700 is similar to apparatus 600 except that it is configured for independent and/or simultaneous S and T measurements. Instead of the removable door 613, a redirecting mirror 736 may direct the transmitted light 18 away from the optical axis 710A and out of the path of the scattered light 16. A second light receiver 738 that may also be an optical fiber end or collection components may receive the transmitted light 18, simultaneously with the first light receiver, receiving the scattered light 16. The second light receiver 738 may be in well known optical communication with an intensity sensor 38, preferably configured as PDA sensor. This transmittance sensor 38 operates in conjunction with a scattering sensor 42 as explained under FIG. 2. The scattering sensor is in well known optical communication with the first optical receiver 701. A focusing mirror 715 may be positioned in the impinging light 10 path between the light source 732 and the vessel 44 such that the light source 732 may be placed out of the optical axis 710A giving room for structural components that guide and move the aperture segments 709, 711.

Ellipsoidal mirrors 603 and 703 are preferred since they provide refocusing of the scattered light 16 in a single step, which results in minimal deterioration of the scattered light 16. Nevertheless, the scope of second and third embodiment may include other curved mirrors such as parabolic, and/or toroidal mirrors.

Capturing the scattered light 16, in a substantially circumferentially continuous fashion, is accomplished by the combination of cylindrical aperture 609, 611, 709, 711 and mirrors 603, 703 that are circumferentially positioned with respect to the impinging light beam 10. This, in combination with angle selective scattering measurement accomplished by the motored aperture segments 609, 611, 709, and 711, provides maximum signal intensity and signal to noise ratio of the scattered and captured light. Moreover and also due to the motored aperture segments 609, 611, 709, and 711, scatter angle resolution can be selected independently, which may additionally contribute to measurement accuracy as may be well appreciated by anyone skilled in the art.

Figure 8:
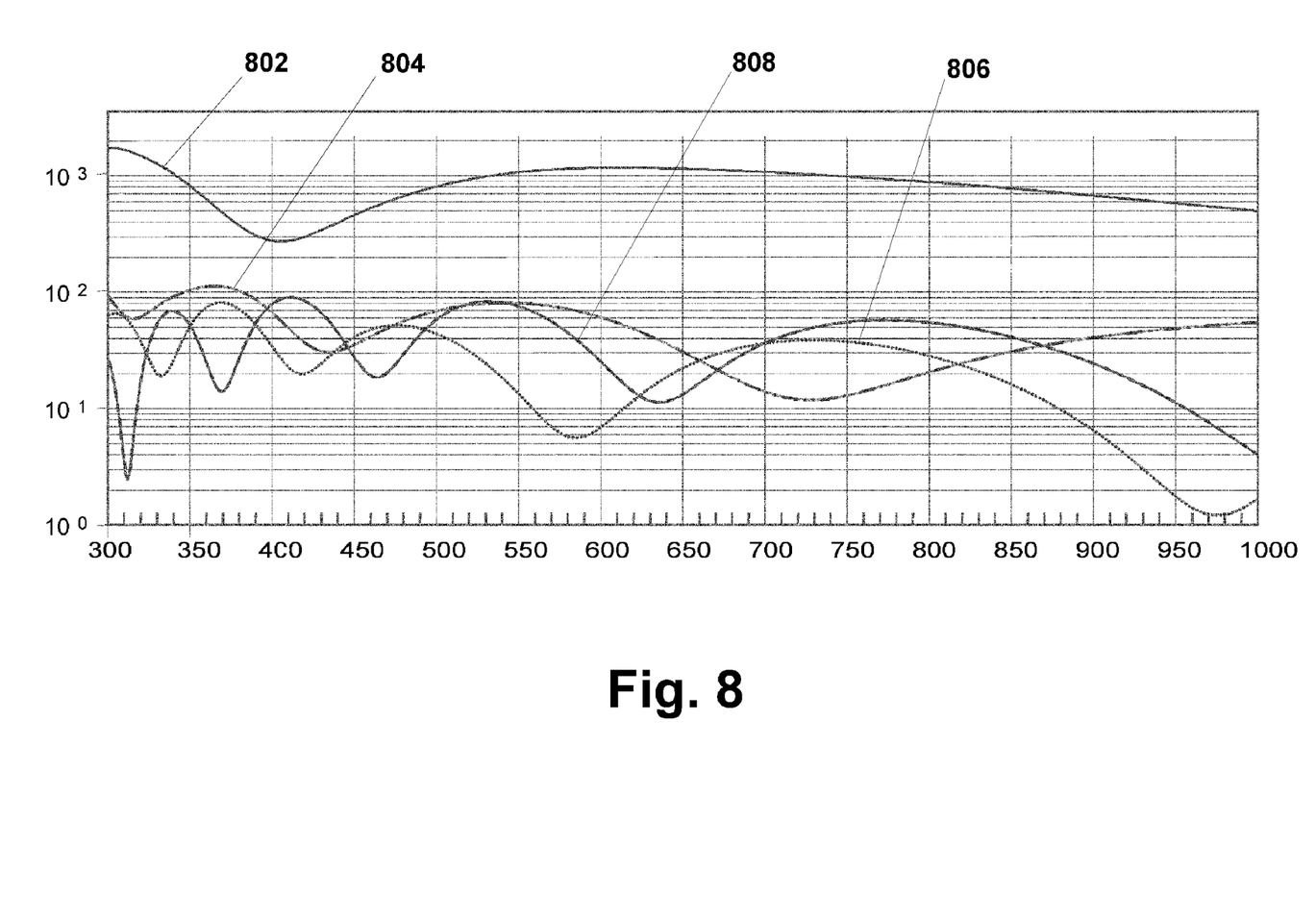
FIG. 8 is a graph of scattering intensities for a 0.5 µm particle size simulated for various scattering angles.
Figure 9:
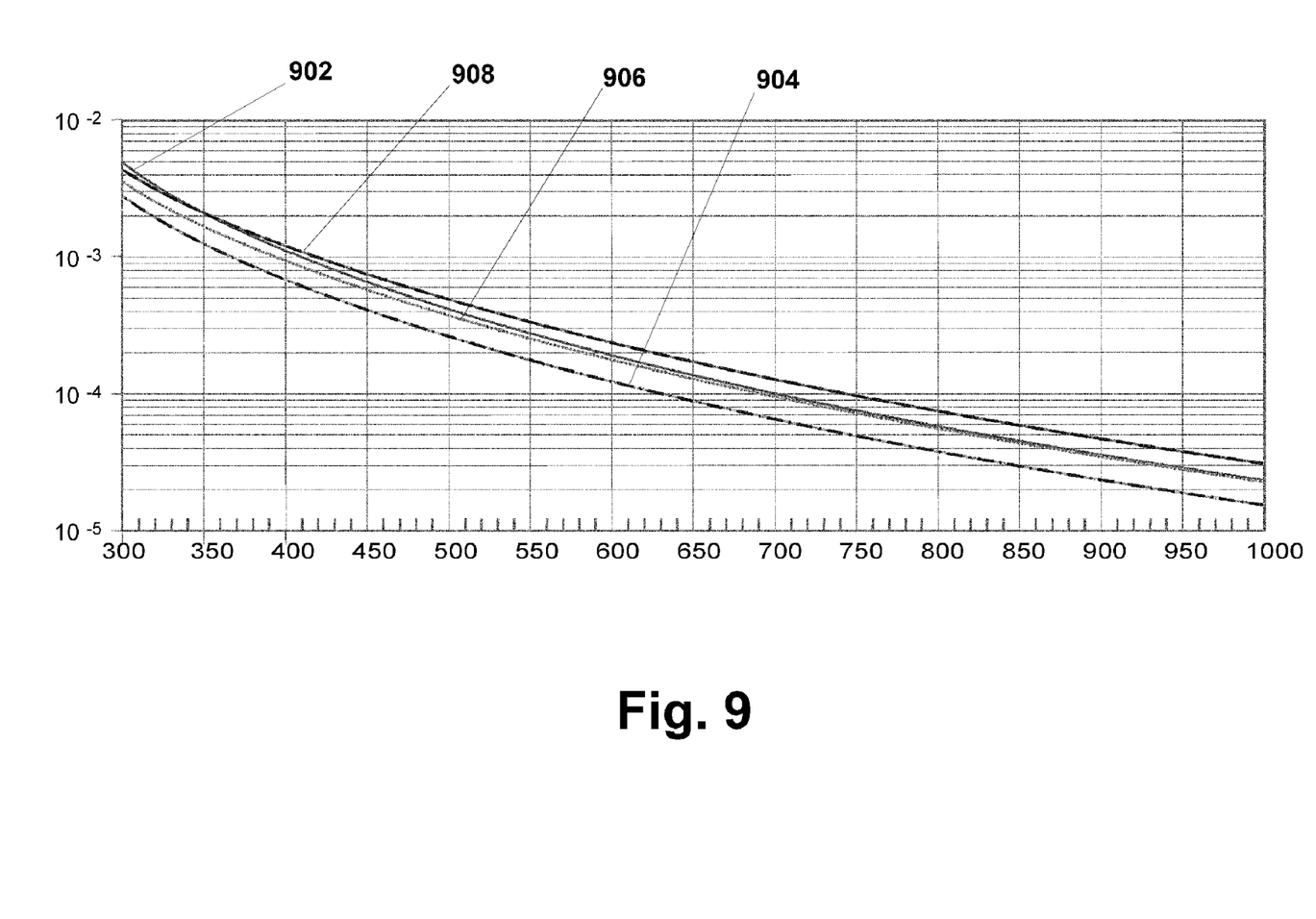
FIG. 9 is a graph of scattering intensities for a 0.05 µm particle size simulated for various scattering angles.
Figure 10:
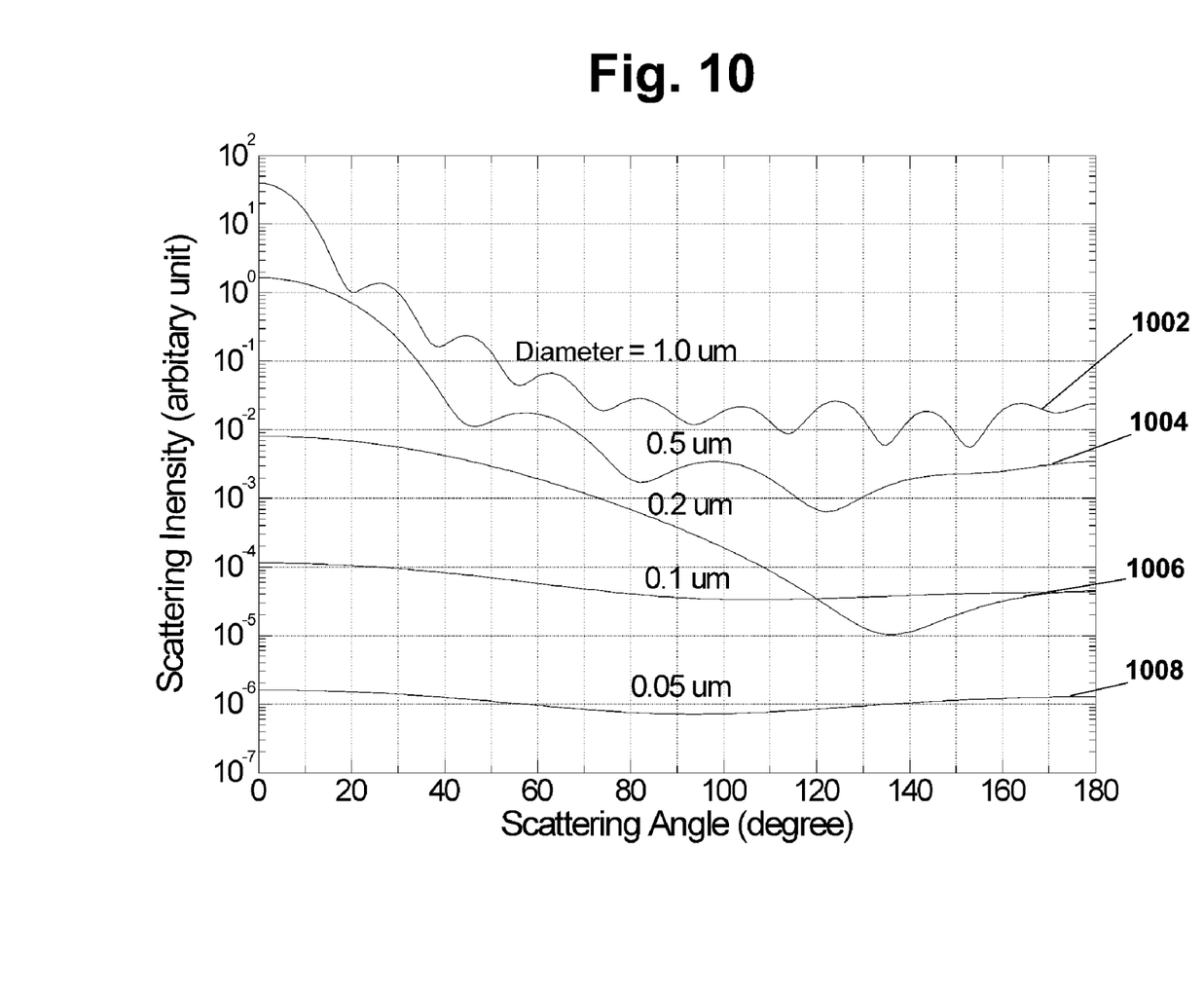
FIG. 10 is a graph of angle dependent scattering intensities for varying particle sizes at a given wavelength.

Simulation results of angular dependent scattering are depicted in FIGS. 8-10. In FIG. 8, curves 802, 804, 806 and 808 illustrate, in an arbitrary unit, the scattering intensities for 0.5 μm PSL suspended in DI water at scattering angles θ of 45, 90, 135 and 180 degrees respectively. In FIG. 9, curves 902, 904, 906 and 908 depict the simulated intensities, also in an arbitrary unit, for 0.05 μm PSL suspended in DI water at scatter angles θ of 45, 90, 135 and 180 degree respectively. It is noted that scattering intensities are higher at shorter wavelength. In FIG. 10, the curves 1002, 1004, 1006 and 1008 show simulated scattering intensities of 1.0, 0.5, 0.1 and 0.05 μm PSL particles at 400 nm wavelength.

Accordingly, the scope of the invention described in the Figures and Specification above is set forth by the following claims and their legal equivalent:

What is claimed is:

1. A device for combined transmittance and angle selective scattering measurement of fluid suspended particles comprising a motorized aperture concentrically positioned with respect to an impinging light beam axis and computer controlled moveable with respect to an impinging light beam axis such that a scattered light emitted from a vessel placed at a focal point of said impinging light beam passes through said motorized aperture in an angle selective fashion that is angle selective with respect to said impinging light beam axis.

2. The device of claim 1, further comprising an ellipsoidal mirror comprising a first focal point and a second focal point, and wherein:

A. said first focal point coincides with a focal point of said impinging light beam along said impinging light beam axis;

B. said second focal point coincides with at least one of an optical fiber end and a receiving component, said at least one of said optical fiber end and said receiving component being in optical communication with a scattering measurement sensor such that said scattering light passing through said motorized aperture is focused by said ellipsoidal mirror at said at least one of said optical fiber end and said receiving component and such that said scattered light is received by said scattering measurement sensor.

3. The device of claim 2 wherein said scattering measurement sensor is a charge-coupled device.

4. The device of claim 2, further comprising a transmittance measurement sensor positioned to receive a transmitted light exiting from a vessel placed at said focal point of said impinging light beam, said transmittance measurement sensor being a photodiode array.

* * * * *